United States Patent [19]

Fay et al.

[11] Patent Number: 5,998,580
[45] Date of Patent: *Dec. 7, 1999

[54] PHOTOSENSITIVE CAGED MACROMOLECULES

[76] Inventors: Frederick F. Fay, 29 Otsego Rd., Worcester, Mass. 01609; Robert Carraway, 17 Brentwood Dr., Holden, Mass. 01520; Mitsuo Ikebe, 1375 Westover Rd., Cleveland Heights, Ohio 44118; Jeffrey Walker, 509 San Juan Ter., Madison, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/542,927

[22] Filed: Oct. 13, 1995

[51] Int. Cl.[6] .......................... A61K 38/00; G01N 33/00; G01N 33/543
[52] U.S. Cl. .......................... 530/333; 530/335; 530/334; 530/336; 530/338; 436/86; 436/518; 930/20
[58] Field of Search ...................................... 530/333, 335, 530/337, 334, 338; 436/86, 518; 930/20

[56] References Cited

U.S. PATENT DOCUMENTS 5,252,743  10/1993  Barrett et al. ......................... 548/303.7
5,406,783   4/1995  Pirrung et al. .......................... 436/518

OTHER PUBLICATIONS

Adams et al., Annu. Rev. Physiol. 55:755–784 (1993).
Denk et al., Science 248:73–76 (1990).
Fodor et al., Science 251:767–773 (1991).
Itoh et al., Nature 338:164–167 (1989).
Lukas et al., Amer. Chem. Soci. 25:1458–1464 (1986).
McCarron et al., Nature 357:74–77 (1992).
McCray, Annu. Rev. Biophys. Chem. 18:239–270 (1989).
V.K. Haridasan et al., Proc. Indian. Natl. Sci. Acad., vol. 53., No. 6., pp. 717–728., 1987.

*Primary Examiner*—Ponnathapura Achutamurthy
*Assistant Examiner*—P. Ponnaluri
*Attorney, Agent, or Firm*—DeWitt Ross & Stevens S.C.

[57] ABSTRACT

Disclosed is a method for preparing a photosensitive peptide which is capable of being activated or deactivated in a biological system, including the steps of: (a) providing an amino acid including a photolabile molecule; and (b) incorporating the amino acid into a peptide during synthesis, wherein incorporation of the amino acid into the peptide produces a photosensitive peptide. Also disclosed is a method of introducing a photosensitive cleavage site into a synthetic peptide, including synthesizing a synthetic peptide having at least one photolabile amino acid, wherein the photolabile amino acid is positioned within the synthetic peptide so that upon irradiation the synthetic peptide is cleaved.

17 Claims, 8 Drawing Sheets

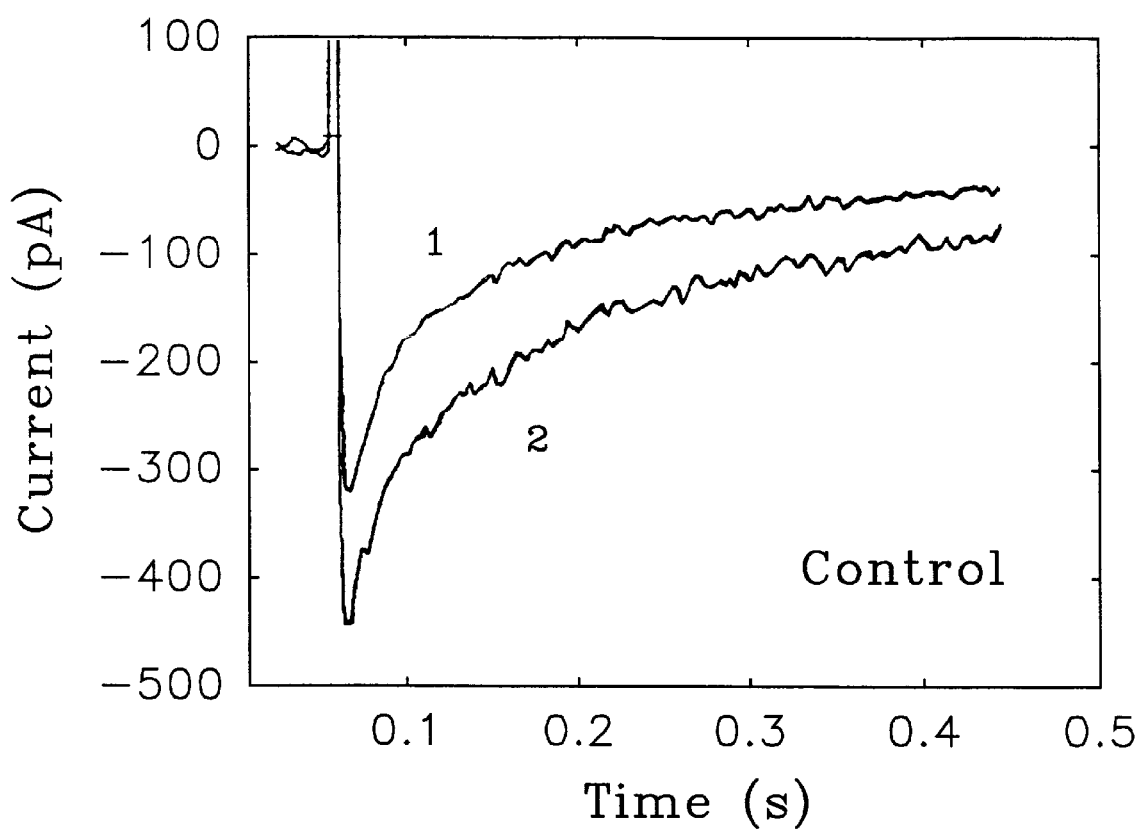

Fig. 4A
NH₂-Ala-Arg-Arg-Arg-Trp-Gln-Lys-Thr-Gly-His-Ala-Val-Arg-Ala-Ale-Gly-Arg-Leu-Ser-Ser-COOH
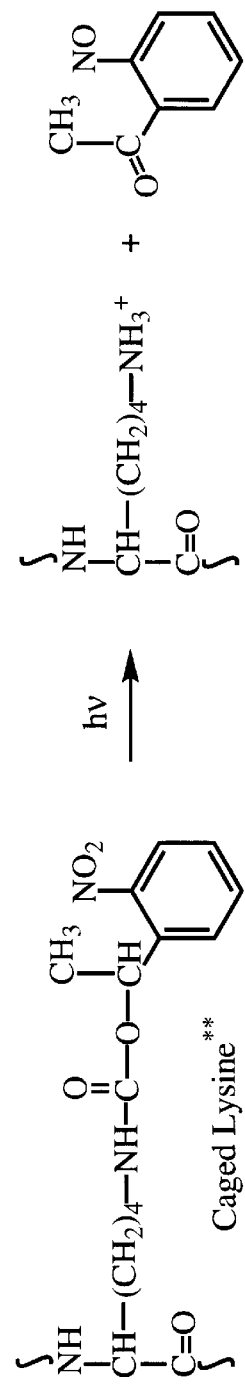
Fig. 4B
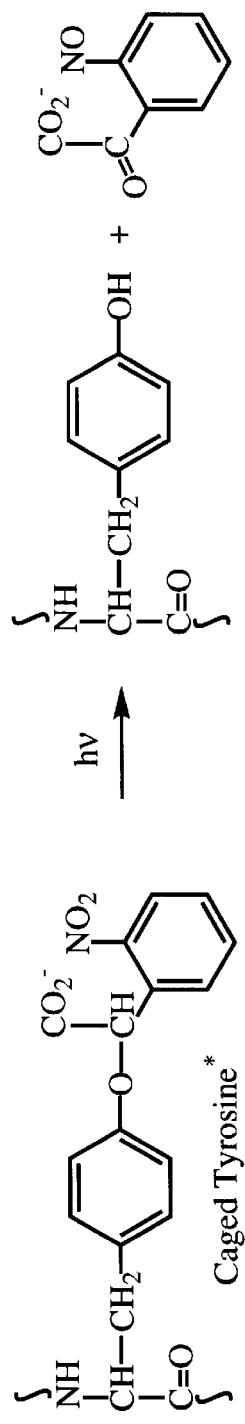
Fig. 4C
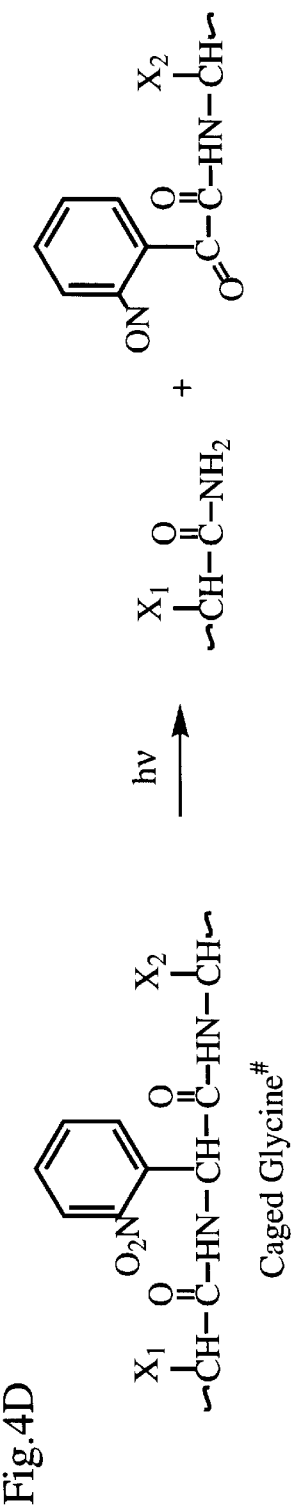
Fig. 4D

PHOTOSENSITIVE CAGED MACROMOLECULES

STATEMENT AS TO FEDERALLY SPONSORED RESEARCH

This invention was made in part with Government funding and the Government therefore may have certain rights in this invention.

BACKGROUND OF THE INVENTION

This invention relates to photosensitive caged molecules, e.g., photosensitive caged peptides.

The development of therapeutic drugs, in general, involves screening natural products or synthetic compounds for substances that affect or interfere with biological processes associated with disease. This random approach was required, in part, by limited knowledge concerning the molecular aspects of such disease processes. Development of molecular genetic techniques has led to the identification of key molecules, e.g., peptides and other small molecules, that regulate normal biological processes, and, in some situations, has defined the cellular pathways responsible for disease. Accordingly, this information can now be exploited and manipulated for the rational design of therapeutic drugs or diagnostic/research agents that specifically target these pathways.

The activity of such molecules can be further controlled and regulated in a specific manner by designing molecules whose biological activity is controlled by light. Such molecules are generally referred to as being "caged." The term caged is utilized as an indication that a biologically active species is trapped inside a larger framework that would be released upon illumination, thus "uncaging" the contents (Adams et al., *Annu. Rev. Physiol.* 55: 755–784, 1993).

For example, attempts have been made to control the activity of biologically active macromolecules, e.g., peptides, using caging chemistry. Initial efforts, however, to modify peptides selectively on amino acid side chains with photolabile protecting groups, have met with only limited success (Adams et al., supra). This is due, in part, to a lack of specificity for a photolabile caging group to specific amino acid residues in the peptide.

SUMMARY OF THE INVENTION

In general, the invention features a method for preparing a photosensitive peptide which is capable of being activated or deactivated in a biological system, including the steps of: (a) providing an amino acid including a photolabile molecule; and (b) incorporating the amino acid into a peptide during synthesis, wherein incorporation of the amino acid into the peptide produces a photosensitive peptide. In preferred embodiments, the amino acid is incorporated into a specific position of the photosensitive peptide. In other preferred embodiments, the photolabile molecule is 2-nitrobenzyloxycarbonyl, α-carboxy 2-nitrobenzyl, and 2-nitrophenyl. In yet other preferred embodiments, the amino acid is lysine, tyrosine, and glycine.

In preferred embodiments, the method of the invention results in the production of a photosensitive peptide that is biologically inactive, yet is capable of being rendered biologically active upon irradiation.

In other preferred embodiments, the method of the invention results in the production of a photosensitive peptide that is biologically active, yet is capable of being rendered biologically inactive upon irradiation.

In another aspect, the invention features a synthetic photosensitive peptide including at least one amino acid having a photolabile molecule in a specific position within the peptide, wherein the photolabile amino acid is introduced into the synthetic peptide during peptide synthesis. In preferred embodiments, the photolabile amino acid of the synthetic photosensitive peptide has the formula

X-Z-Y wherein X is any amino acid which is bonded via its side chain to Z, Z is

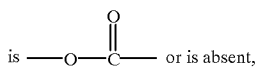

or is absent, and Y has the formula

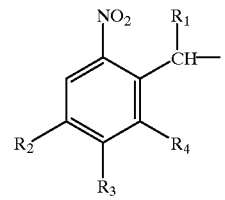

wherein, independently, $R_1$ is —H, —CH$_3$, —CONH$_2$ or —COO$^-$; $R_2$, $R_3$, and $R_4$ are, independently, —H, —CH$_3$, —OCH$_3$, —CH$_2$COO$^-$, —OH, or —NO$_2$.

In preferred embodiments, the photolabile amino acid is 2-nitrophenyl glycine (NPG) and 0-α-carboxyl-2-nitrobenzyl tyrosine (cTyr).

In another aspect, the invention features a method of introducing a photosensitive cleavage site into a synthetic peptide, including synthesizing a synthetic peptide having at least one photolabile amino acid, wherein the photolabile amino acid is positioned within the synthetic peptide so that upon irradiation the synthetic peptide is cleaved.

In preferred embodiments, the photolabile amino acid residue has the formula

X-Z-Y wherein X is any amino acid which is bonded via its side chain to Z, Z is

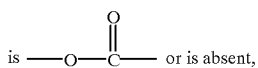

or is absent, and Y has the formula

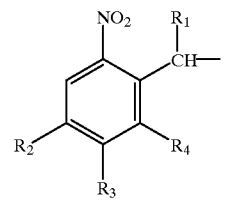

wherein, independently, $R_1$ is —H, —CH$_3$, —CONH$_2$ or —COO$^-$; $R_2$, $R_3$, and $R_4$ are, independently, —H, —CH$_3$, —OCH$_3$, —CH$_2$COO$^-$, —OH, or —NO$_2$.

Preferably, the photolabile amino acid is 2-nitrophenyl glycine (NPG).

In yet another aspect, the invention features a self-cleaving photosensitive synthetic peptide including at least one photolabile amino acid having a photolabile molecule, wherein the photolabile amino acid is positioned within the synthetic peptide so that upon irradiation the synthetic peptide is cleaved.

In preferred embodiments, the photolabile amino acid has the formula

X-Z-Y wherein X is any amino acid which is bonded via its side chain to Z, Z is

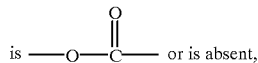

or is absent, and Y has the formula

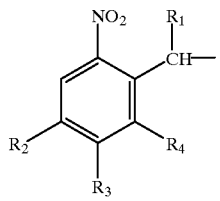

wherein, independently, $R_1$ is —H, —$CH_3$, —$CONH_2$ or —$COO^-$; $R_2$, $R_3$, and $R_4$ are, independently, —H, —$CH_3$, —$OCH_3$, —$CH_2COO^-$, —OH, or —$NO_2$.

Preferably, the photolabile amino acid is 2-nitrophenyl glycine (NPG).

In another aspect, the invention features a method of activating a photosensitive peptide in vivo, the method including: (a) administering a therapeutically effective amount of a photosensitive peptide to a patient; and (b) administering a dose of irradiation to the patient in a dosage sufficient to biologically activate the photosensitive peptide.

In another aspect, the invention features a method of deactivating a photosensitive peptide in vivo, the method including: (a) administering a therapeutically effective amount of a photosensitive biologically active peptide to a patient; and (b) administering a dose of irradiation to the patient, in a dosage sufficient to biologically deactivate the photosensitive peptide.

In another aspect, the invention features a method of inhibiting a neoplasm in a patient using a photosensitive peptide, the method including: (a) administering a therapeutically effective amount of a photosensitive peptide to a patient, wherein the peptide, in an uncaged form inhibits the neoplasm; and (b) administering a dose of irradiation to the patient, in a dosage sufficient to uncage the photosensitive peptide wherein the activated photosensitive peptide inhibits the neoplasm.

In another aspect, the invention features a method of inhibiting a signal transduction pathway in a patient using a photosensitive peptide, the method including: (a) administering a therapeutically effective amount of a photosensitive peptide to a human patient; and (b) administering a dose of irradiation to the patient, in a dosage sufficient to activate the photosensitive peptide wherein the activated photosensitive peptide inhibits a signal transduction pathway.

As set forth above, and for convenience in describing this invention, conventional and nonconventional abbreviations for the various amino acids are used. All peptide sequences mentioned herein are written according to the usual convention whereby the N-terminal amino acid is on the left, and the C-terminal amino acid is on the right. A short line between two amino acid residues indicates a peptide bond.

The compounds of the present invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids, such as hydrohalic acids, e.g., hydrochloric acid, sulfuric acid, or phosphoric acid and the like.

In preferred embodiments, the composition is in the form of a liquid, pill, tablet, or capsule for oral administration; a liquid capable of being administered nasally as drops or spray, or a liquid for intravenous, subcutaneous, parenteral, intraperitoneal, or rectal administration. The therapeutic composition can also be in the form of an oil emulsion or dispersion in conjunction with a lipophilic salt such as pamoic acid, or in the form of a biodegradable sustained-release composition for subcutaneous or intramuscular administration. Delivery of the composition of the invention can also be achieved using liposome technology. For maximum efficacy, zero-order release is desired.

By "peptide" is meant any chemical compound having more than one amino acid. Accordingly, the term encompasses polypeptides and proteins.

By "photosensitive" is meant capable of becoming biologically active or biologically inactive upon exposure to radiant energy.

By "biologically active" is meant a having physiological or therapeutic activity. By "biologically inactive" is meant having diminished physiological or therapeutic activity.

The compositions and methods of the invention are advantageous in a number of aspects. For example, photosensitive peptides and derivatives thereof of the invention are advantageous in that they are biocompatible, lack deleterious side effects, and are suitable for different forms of therapeutic administration. In addition, the compounds and methods of the invention allow delivery of therapeutic compositions to discrete regions of the body by virtue of the ability to activate peptides by a focused beam of irradiation, e.g., ultraviolet or infrared. In addition, the methods of the invention provide for rapid and localized release of biologically active compounds from biologically inactive precursors.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patents, and patent applications mentioned herein are incorporated by reference. In addition, the materials, methods, and examples are illustrative only and not intended to be limiting.

Other features and advantages of the invention will be apparent from the following detailed description, and from the claims.

DETAILED DESCRIPTION

The drawings will first be described.

Drawings

Figure 3B:
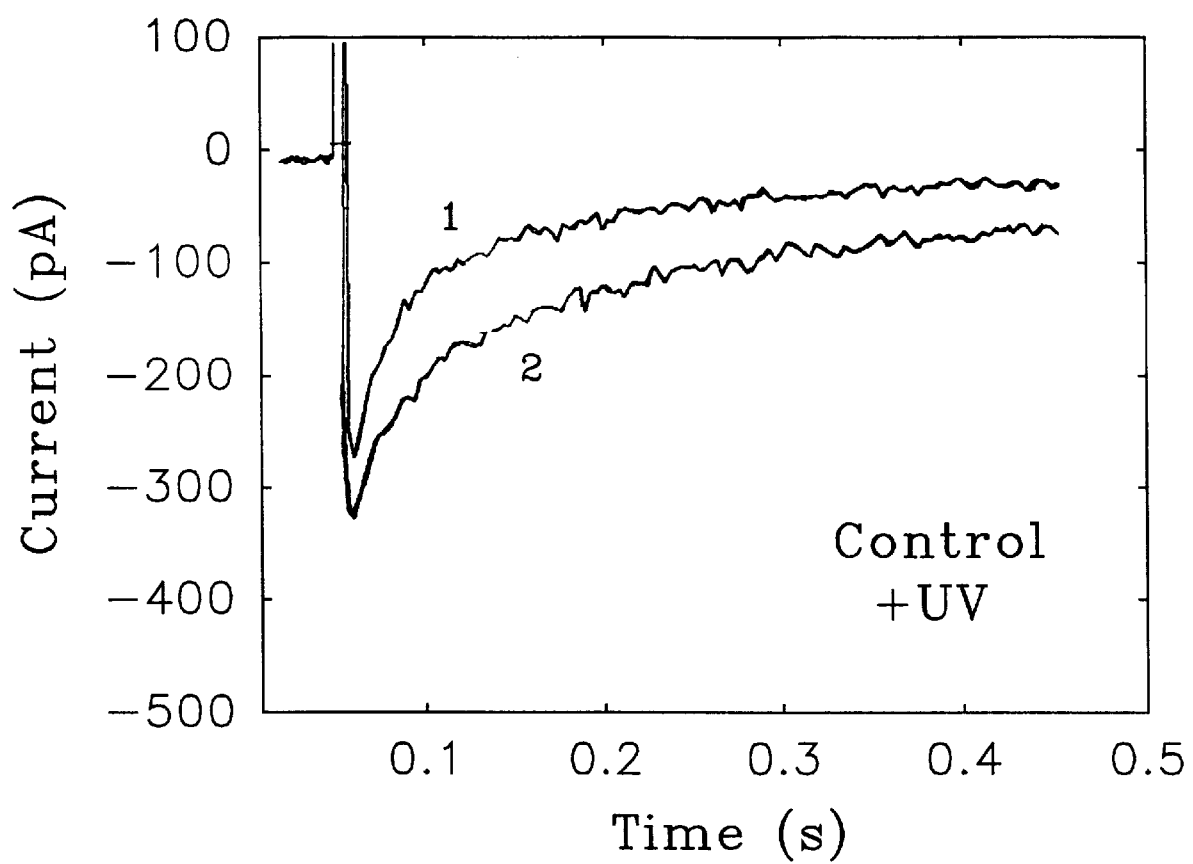
Figure 3C:
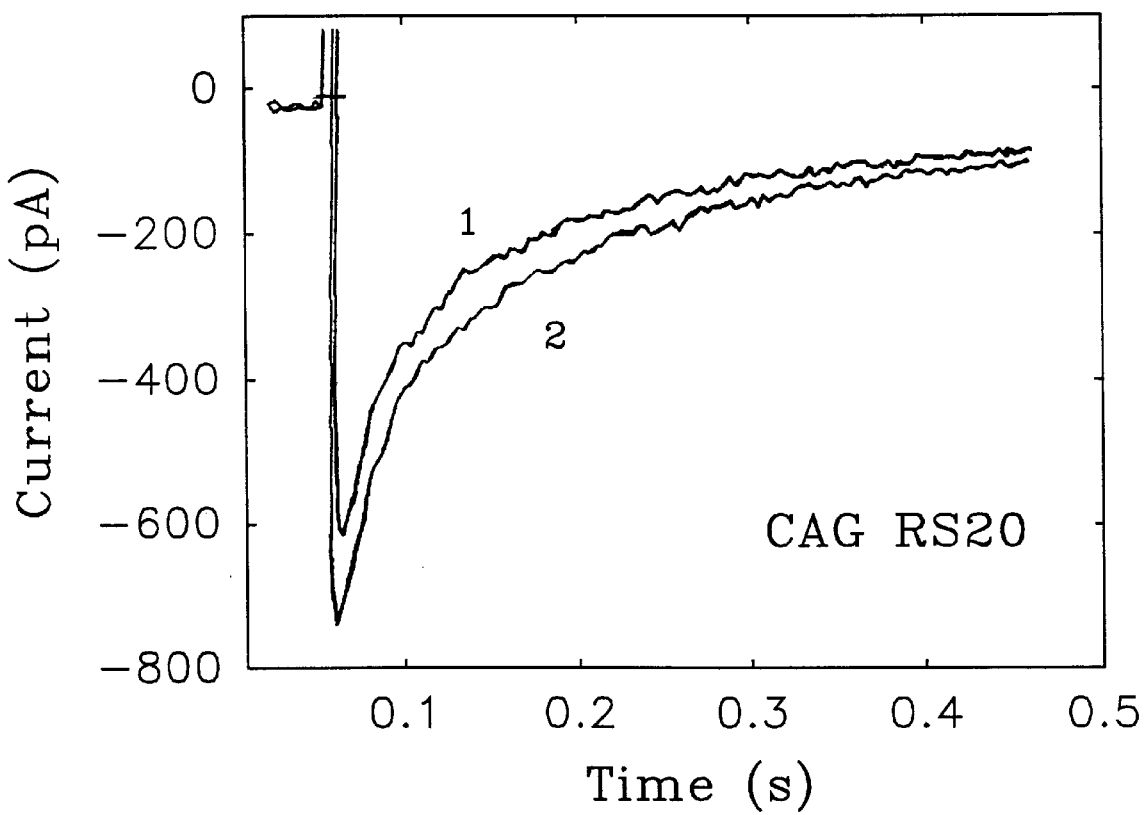
Figure 3D:
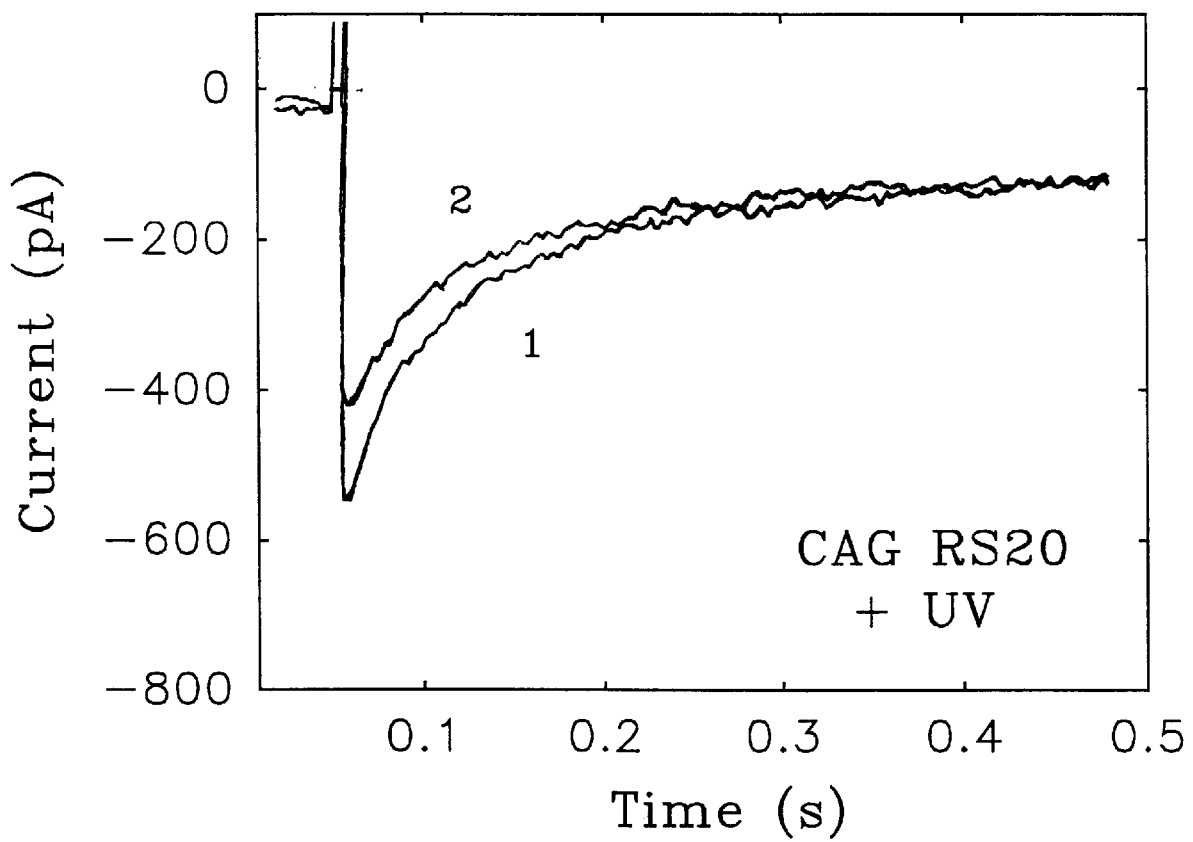

FIGS. 3A to 3D are a series of graphs showing the effects of the caged $Ca^{2+}$-calmodulin inhibitory peptide, 1-CAG-RS-20, on the enhancement of inward current following repetitive depolarization in single smooth muscle cells. FIGS. 3A and 3B, respectively, show the results of pre- and post-UV exposure control tests without peptides. FIGS. 3C and 3D, respectively, show the results of pre- and post-UV exposure of 1-CAG-RS-20.

FIGS. 4A to 4D are a series of schematic illustrations showing the amino acid sequence of the $Ca^{2+}$-calmodulin inhibitory peptide RS-20 (FIG. 4A) and various caged amino acids (FIGS. 4B–D). FIG. 4A shows the primary structure of RS-20. The symbols *, †, and ⊕ denote positions for introducing caged amino acids. FIGS. 4B–4D show the respective structures of the photosensitive caged amino acids lysine, tyrosine, and glycine, and their photoreleased products upon photolysis.

Figure 5:
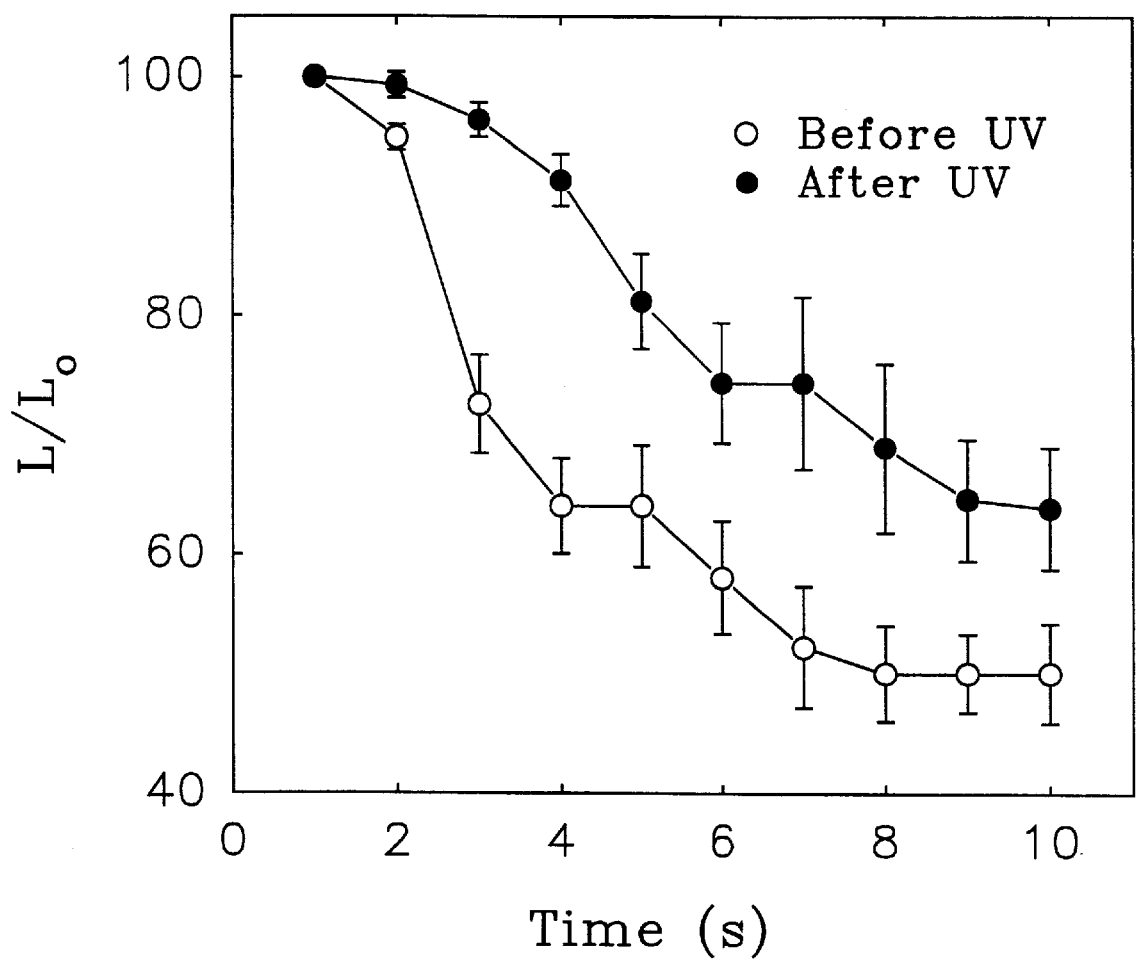

FIG. 5 is a graph showing the effect of photolysing the caged $Ca^{2+}$-calmodulin inhibitory peptide, 1-CAG-RS-20, on the rate of shortening of single smooth muscle cells both before and after UV illumination.

OVERVIEW

The present invention provides methods for synthesizing virtually any number of photosensitive biological molecules and for using such molecules in vivo, ex vivo, and in vitro. For example, the methods of the invention are generally applicable to a variety of classes of compounds and molecules which include, but are not limited to, enzymes, amino acids, reiterated protein binding domains (e.g., leucine zippers and zinc fingers) that are involved in intracellular signalling pathways, DNA regulatory elements, nucleotides, substrates, cofactors, immunoglobins, antibodies, haptens, antigens, oligonucleotides, oligosaccharides, proteins, peptides, glycoproteins, lipid mediators, neurotransmitters, hormones, cytotoxins, adhesion molecules, immunosuppressive or immunostimulatory agents, chemotherapeutic agents, and organic compounds.

In general, the methods of the invention make use of photosensitive or photolabile protecting groups, i.e., caging groups, which have been specifically engineered onto the backbone of a biological molecule as a means to inactivate or alter or modify their biological activity upon exposure to the appropriate irradiation. Accordingly, the biological activity of these caged or photosensitive molecules is controlled by irradiation, e.g., infrared or ultraviolet. The approach generally involves chemical modification of a molecule or compound, e.g., a peptide, so that the biological activity can be activated or eliminated upon exposure to light. This approach provides a means for regulating biological activity of the caged compound, e.g., by producing or destroying biological activity, at any desired time in a highly localized manner. The timing depends upon several factors such as the chemical and biological stability of both photosensitive and photoreleased agents in the biological environment, and the characteristics of the irradiating light including its shape, tissue penetrability, and the duration of exposure.

Photosensitive Caged Peptides

The photosensitive peptides of the present invention can be synthesized by techniques that are known to those skilled in the peptide art. The general strategy for producing a photosensitive caged peptide is to provide, e.g., by chemical synthesis, one or more caged amino acids or caged amino acid derivatives, and then to insert such an amino acid into one or more positions of the growing peptide during peptide synthesis, e.g., solid phase peptide synthesis. Such caged amino acids are generally incorporated into a peptide to alter, modify, or eliminate biological activity. Positioning of a caged amino acid as a means for modifying biological activity of a peptide is determined according to standard methods known in the art.

In one working example, the position into which a caged amino acid is to be inserted in a peptide is determined by employing structure-function based studies, e.g., by synthesizing variants of a peptide in which one or more amino acids are either altered, deleted, or modified to disrupt interactions of the amino acid or a series of amino acids with a target structure, or by defining the sites of contact between interacting proteins. For example, a positively charged amino acid such as lysine can be substituted for a negatively charged amino acid such as glutamic acid, or a hydrophobic amino acid such as tyrosine can be substituted for a charged non-hydrophobic amino acid such as glutamic acid. By analyzing the effects of these modifications, one can determine which amino acids are involved in the normal action of a peptide, and then make modifications of specific amino acids using photolabile caging groups that alter the ability of a given amino acid to form an interaction, e.g., an ionic or hydrophobic interaction, with its targets, e.g., as is described below.

Further information regarding the importance of a specific amino acid, or a peptide having a short sequence of contiguous amino acids, for interaction with target molecules can, of course, be obtained by structural methods including, but not limited to, high-resolution X-ray crystallography or nuclear magnetic resonance (NMR) structural analyses and computational methods, according to methods known in the art.

For example, activation of an inhibitor of a biological pathway, e.g., protein-protein interactions that are involved in all stages of signal transduction process, can be developed by structure-based strategies that involve the design of small organic molecules, e.g., a caged peptide, that mimics the structure of a binding site. Thus, activation of a particular pathway could be modulated by designing a small caged molecule that specifically disrupts one of the receptor target interactions upon illumination.

There now follows a description of the methods useful for modifying amino acids with photosensitive caging groups.
Synthesis of Photosensitive Amino Acid Derivatives In general, the strategy for preparing a photosensitive caged amino acid involves protecting the α-amino group, e.g., with BOC (butyloxycarbonyl), and the α-carboxyl group, e.g., with a t-butyl ester, followed by reacting the amino acid side chain with a photolabile caging group, e.g., 2-nitrobenzyl, in a reactive form, e.g., 2-nitrobenzylchloroformate, α-carboxyl 2-nitrobenzyl bromide methyl ester, or 2-nitrobenzyl diazoethane. Examples of a variety of photolabile protecting groups useful in the invention are discussed below and are shown in Table I (below).

Following the modification of the amino acid with a photolabile caging group, the amino and carboxyl protecting groups are removed according to standard methods, e.g., using neat trifluoroacetic acid (TFA), and the derivatized amino acid is converted to an Fmoc form for peptide synthesis, e.g., caged amino acids are converted to the Fmoc form using Fmoc succinimide according to methods known in the art (TenKortenaar et al., *Int. J. Peptide Protein Res.* 27: 398–400, 1986).

As discussed below, lysine residues can be caged using 2-nitrobenzylchloroformate to derivatize the ε-lysine amino group and thereby eliminate the positive charge or by introducing a negative charge into the peptide by use of an α-carboxy 2-nitrobenzyloxycarbonyl caging group. The α-carboxyl group is protected as a methyl ester during all steps including amino acid synthesis and peptide synthesis. Phosphoserine and phosphothreonine can be caged by treatment of the phosphoamino acid or the phosphopeptide with 1(2-nitrophenyl)diazoethane (Walker et al., *Meth Enzymol.* 172: 288–301, 1989). A variety of other amino acids are also readily accessible to standard caging chemistry including but not limited to serine, threonine, histidine, glutamine, asparagine, aspartic acid and glutamic acid (Wilcox et al., *J. Org. Chem.* 55:1585–1589, 1990).

Amino acid residues can also be made photosensitive or photolabile in such a way that irradiation causes cleavage of the peptide backbone at that residue rather than an uncaging of that amino acid residue. An example of this is a photolabile glycine, 2-nitrophenyl glycine, prepared as described (Davis, A. L., Smith, D. R. and McCord, T. J. (1973) *J. Med. Chem.* 16:1043–1045). Irradiation of peptides containing 2-nitrophenylglycine cleaves the peptide backbone between the alpha carbon and the alpha amino group of 2-nitrophenylglycine. This strategy is generally applicable to any amino acid other than glycine if the 2-nitrobenzyl group is inserted between the alpha carbon and the alpha amino group.

Photosensitive Caging Groups

A variety of photosensitive caging groups can be used for modifying and controlling the biological activity of the compounds of the present invention. In general, caging groups inhibit or conceal (e.g., by disrupting bonds that normally stabilize an interaction with a target molecule, by modifying the hydrophobicity or ionic character of a particular side chain in a peptide, or by steric hindrance) an important property necessary for biological activity, e.g., an active site or a folding pattern, or any combination thereof. Destruction of the caging group modifies the molecule, e.g., rendering it active or inactive.

The selection of a suitable caging group is dependent upon the size and chemical nature of the group selected, and will be readily apparent to one skilled in the art. For example, a caging group should render a peptide of the invention inert to the biological system, and photolyse at wavelengths non-detrimental to the biological system. Furthermore, the by-products of photolysis should not interfere or interact with the biological system in a detrimental manner.

There is a wide array of photochemical protecting groups known to those in the art (Merrifield, *Science* 232:341 (1986) and Corrie, J. E. T. and Trentham, D. R. (1993) In: Biological Applications of Photochemical Switches, ed., Morrison, H., John Wiley and Sons, Inc. New York, pp. 243–305). Examples of suitable photosensitive caging groups include, but are not limited to, 2-nitrobenzyl, benzoin esters, N-acyl-7-nitindolines, meta-phenols, and phenacyls. Examples of such photosensitive or photolabile caging groups, derivatives, and corresponding wavelengths for deprotection are provided in Table I.

TABLE I

PHOTOLABILE PROTECTING GROUPS FOR USE WITH PHOTOSENSITIVE PEPTIDES

CLASS I

| | |
|---|---|
| Common Name | 2-nitrobenzyl |
| Generalized Structure: | [structure: benzene ring with $NO_2$, $R_1$, $R_2$, $R_3$ substituents and C group] |
| Common Substituents: | $R_1$ = H, —$CH_3$, —$COO^-$<br>$R_2$, $R_3$ = H, —$CH_3$, —$OCH_3$, —$CH_2COO^-$, —OH |
| Other Important Variations: | [structure with $NO_2$, $R_1$, CH—O—C(=O)— group] |
| | Oxocarbonyls |
| | [dinitro structures with $NO_2$ groups, $R_1$, $R_2$, $R_3$] |
| | dinitros |
| Photolysis Wavelength: | 300–360 nm |

Reference: Corrie and Trentham 1993 (supra)

CLASS II

| | |
|---|---|
| Common Name | benzoin esters |
| General Structure: | [structure: benzoin ester with $OCCH_3$ group and R substituents] |

TABLE I-continued

PHOTOLABILE PROTECTING GROUPS FOR USE WITH PHOTOSENSITIVE PEPTIDES

| | |
|---|---|
| Common Substituents: | R = H, —OCH$_3$, —CH$_3$ |
| Photolysis wavelength: | 350 nm |

Reference: Sheehan and Wilson, 1964, J. Amer. Chem. Soc. 86:5277

CLASS III

| | |
|---|---|
| Common Name | N-Acyl-7-nitroindolines |
| General Structure: | [structure of 7-nitroindoline with X substituent] |
| Common Substituents: | X = Br, NO$_2$ |
| Important Variations: | [structure of N-acyl-8-nitrotetrahydro-quinoline with X substituent] |
| | N-acyl-8-nitrotetrahydro-quinolines |
| Photolysis Wavelength: | >400 nm |

Reference: Amit, Ben-Efraim, and Patchornik, 1976, J. Amer. Chem. Soc. Perkin I 57

CLASS IV

| | |
|---|---|
| Common Name | meta-phenols |
| General Structure: | [structure of phenol with R$_1$ and R$_2$ substituents] |
| Common Substituents: | R$_1$ = NO$_2$, H, —OCH$_3$, R$_2$ = H, —OCH$_3$ |
| Photolysis wavelength: | 350 nm |

Reference: Chamberlin, 1966, J. Org. Chem 31:1658

CLASS V

| | |
|---|---|
| Common Name | Phenacyl |
| General Structure: | [structure of phenacyl group with R substituent] |
| Common Substituents: | R = H, —OCH$_3$ |
| Photolysis wavelength: | 350 nm |

Reference: Sheehan and Umezawa, 1973, J. Org. Chem. 38:3771

Synthesis of Photosensitive Caged Peptides

The photosensitive peptides of the present invention can be synthesized by techniques that are known to those skilled in the peptide art. Excellent descriptions of the many techniques available are found in Merrifield, *J. Amer. Chem Soc.* 85: 2149–2154, 1963; *Solid Phase Peptide Synthesis* 2nd ed. (Stewart, J. M. and Young, J. D. Pierce Chemical Company, Rockford, Ill., 1984), and Atherton et al., *J. Chem. Soc. Commun.* 165–66, 1985. In general, the photosensitive caged peptides of the invention are synthesized by solid-phase methods using Boc- or Fmoc-forms of a photosensitive caged amino acid (supra) in combination with a resin, e.g., a styrene divinyl benzene resin, on which the peptide is constructed. Such processes, if desired, can be automated using instruments available from Rainin Instrument Co. (Woburn, Mass.), Millipore Corp. (Milford, Mass.), Gilson Inc. (Middleton, Wis.), or Applied Biosystems (Foster City, Calif.).

Fmoc methods are known to those skilled in the art, see, e.g., Atherton et al., *Solid Phase Peptide Synthesis: A Practical Approach*, IRL Press, 1989; Fields et al., *Synthetic Peptides: A User's Guide*, Grant, G. A., ed., W. H. Freeman and Co., New York, pp: 77–183, 1992; and Fields et al., *Int. J. Peptide Protein Res.* 35: 161–214, 1990). The basic Fmoc method, in general, involves performing repetitive cycles of coupling the activated C-terminus of a Fmoc-amino acid to the N-terminus of the growing resin-linked peptide chain. Reactive side-chains are blocked with stable protecting groups, e.g., t-butyl ether (used to block Ser, Thr, Tyr), t-butyl ester (used to block Asp, Glu), trityl (used to block His, Cys, Asn, Gln), or butyloxycarbonyl (used to block Lys). At the completion of synthesis, protecting groups are removed as the peptide is cleaved from the resin (e.g., using a strong acid such as TFA). Upon cleavage, photosensitive caged peptides are recovered using standard methods, e.g., by using diethyl ether, and purified according to standard methods, e.g., reverse-phase HPLC. Confirmation of the identity of the synthesized compounds is determined by conventional techniques such as microsequencing, NMR, amino acid analysis, and mass spectrometry.

Cyclization

Photosensitive caged cyclic peptides of the invention are prepared according to standard methods by introducing a derivatized photolabile amino acid, e.g., nitrophenyl glycine (NPG), into the peptide chain during peptide synthesis using standard Boc- and Fmoc strategies. The basic method involves preparing a form of peptide having all reactive side chains blocked, and having free N- and C-termini. For example, this is accomplished by employing a Fmoc strategy using a resin with a linkage that is labile to a weak acid, e.g., a chloro-trityl resin (NovaChem, Calif.) which is sensitive to acetic acid.

After cleavage from the resin, which frees the C-terminus while maintaining the side chains blocked, the peptide is cyclized in a dilute solution using various activating agents (e.g., benzotriazol-1-yloxytris(dimethylamino)

phosphonium hexaflurophosphate (BOP), benzotriazol-1-yl-oxytris(pyrrolidinol)phosphonium hexaflurophosphate (PyBOP), 0-benzotriazol-1-yl, N,N,N',N'-tetrametyluronium hexaflurophosphate (HBTU), 2-(1H-benzotriazol-1-yl)-1,1,3,3-tetramethyluronium-tetrafluoroborate (TBTU), diphenyl-phosphorylazide (DPPA). Other possible schemes include, but are not limited to, peptide cyclization on an oxione resin (Osapay et al., Peptide cyclization on an oxine resin (the PCOR method) in: *Techniques in Protein Chemistry II*, Academic Press Inc., San Diego Calif., 1991, pp. 221–231), and by head to tail cyclization using an allyloxycarbonyl blocking group (Kates et al., in *Peptides: Chemistry Structure & Biology*, ESCOM, Leiden, 1994, p. 113, and H. Kunz et al., *Int. J. Peptide Protein Res.*, 26: 493, 1995).

In one working example, the α-amino group of the N-terminal residue is liberated by removal of the Fmoc group and a side chain group (e.g., Asp or Glu) will be liberated by Pd(0) treatment of an allyl ester protected Asp or Glu in the peptide. Intramolecular cyclization between the N-terminus and carboxyl side chain is then catalyzed by treatment with BOP or a related reagent known in the art. The photosensitive cyclic peptide is then released from the solid support, deprotected, and purified by standard procedures.

Irradiation with light (see below) releases a side chain residue that is critical for activity or, as in the case of NPG, is used as a means for cleaving the peptide backbone in such a way to open the cyclic peptide to a linear peptide with different biological properties.

Photoactivation

Activation of a caged peptide is accomplished by destruction of a photosensitive caging group by any standard method known to those skilled in the art. For example, a photosensitive peptide is uncaged upon exposure to any suitable conventional light source. Examples of such light sources include, without limitation, (1) lasers (e.g., excimer lasers) emitting energy in the ultraviolet portion of the spectrum or (2) lasers (e.g., diode, Ti:sapphire lasers, holmium lasers (and other rare earth metal lasers), neodynium (Nd) YAG, Nd YAG lasers) emitting radiation in the infrared portion of the spectrum, and which produce brief, high flux density emissions. If desired, pulsed irradiation, which is useful in generating two-photon excitation, can be generated by standard optical modulation techniques known in the art, such as by employing mode-locked lasers (using, for example, electro or acousto-optic devices). Lasers that operate in a pulsed mode in the infrared, visible, and near-infrared spectrum include Nd:YAG, Nd:YLF, $CO_2$, excimer, dye, Ti:sapphire, diode, holmium (and other rare-earth materials), and metal-vapor lasers. The pulse widths of these light sources are adjustable, and can vary from several tens of femtoseconds to several hundred microseconds.

In general, lasers are preferable sources of irradiation because they provide well defined spatially coherent wavelengths of irradiation particularly suited for uncaging of photosensitive caging groups in defined regions. Furthermore, such light sources can be delivered by optical fibers and used to irradiate a specific region in a controllable manner. Fiber optic delivery systems are particularly maneuverable, and can be used to irradiate a region of the body, e.g., a tissue, thereby generating irradiation in hard to reach places. These types of delivery systems, when optically coupled to lasers, are useful as they can be integrated into catheters and related flexible devices, and used to irradiate virtually any organs or region in the human body. In addition, the wavelength of the optical source can be easily tailored to generate the appropriate absorption in a particular cell or tissue type; this allows a number of different cells or tissues to be effectively treated using the compounds and methods of the invention.

Photolysis of photosensitive caged peptides affords a means of controlling the release, both spatially and temporally, of biologically active peptides. In particular, photolysis of caged peptides of the invention can be localized with precision to discrete regions of a cell or tissue of the body by virtue of the ability to activate the caged product using a focused beam of irradiation, e.g., ultraviolet or infrared irradiation. In the latter case, it is useful to employ high flux densities for facilitating two photon excitation (Denk et al., *Science* 248: 73–76, 1990), which is particularly advantageous for photodynamic therapies employing the caged peptides of the invention, because the tissues of the body are virtually opaque to ultraviolet radiation but transparent to infrared radiation. This method allows beams of light to be focused within the body, thereby controlling reactions at specific sites. A further advantage of two photon excitation methodologies is that the probability of photoactivation of a compound is a function of the square of the distribution of illumination intensity giving rise to a highly defined region for activation. Moreover, the ability of two photon excitation to utilize light in the infrared portion of the spectrum is advantageous since it provides the opportunity to use a wide range of wavelengths that are transmitted within the body.

Testing

Those skilled in the art of peptide chemistry and therapeutics will understand that any of a variety of conventional assays can be used for evaluating and testing the efficacy of a photosensitive caged peptide, e.g., those assays described herein. A wide range of cellular or tissue functions can be assayed following the introduction of the caged peptide into the cell or tissue before versus after irradiation with a light source in vivo or in vitro as described herein.

Recent analysis of structure-function relationship of diverse proteins; including but not limited to, membrane receptor proteins and enzymes, has revealed that small domains of proteins characterized by short peptide sequences (e.g., 20 amino acid residues) impose functions such as ligand-binding, protein-protein interaction, and regulation of enzymatic activity, among others. Accordingly, if a short peptide which is synthesized to duplicate or mimic a functional domain of a protein is fully functional then its biological activity can be controlled.

For example, short peptides synthesized according to the calmodulin binding domain or the autoinhibitory domain of calmodulin-dependent protein kinases have been shown to inhibit protein kinase activity. While such short peptides themselves do not form a stable three-dimensional structure, such peptides are thought to be capable of assuming a specific biologically active conformation upon interaction with a target protein. Thus, inhibiting a peptide from forming a biological active conformation (e.g., according to the methods described herein) would be expected to result in a loss of biological activity of that peptide. Accordingly, the effects of caging and uncaging of the molecule can be monitored in vitro and in vivo by measuring the biological activities of a target protein. For example, the activity of a peptide which mimics the calmodulin binding domain of calmodulin dependent protein kinases is determined by measuring calmodulin binding activity determined by the change in fluorescence of fluorescently labelled calmodulin or by measuring the inhibition of the calmodulin dependent protein kinase activity due to the depletion of calmodulin by such a peptide or by both methods.

Photodynamic Therapy

Photosensitive caged peptides and derivatives thereof prepared according to the methods of the invention have a variety of uses well known to those skilled in the art. The caged peptides of the invention can be used to treat a mammal, e.g., a human, suffering from a variety of medical disorders, e.g., cancer. In general, such photosensitive molecules are used to specifically interfere with critical molecular interactions that underlie disease processes.

The generation of caged peptides derived from structural analysis of protein interaction sites, e.g., as described above, provides a straightforward strategy for rational drug design of substances useful in photodynamic therapies. Application of such technology to human disease therapy provides a precise method for designing a therapeutic agent that does not block all interactions involving a class of protein domains. For example, photodynamic therapeutic agents of the invention can be designed to stimulate, modify, alter, or disrupt virtually any molecular interaction, e.g., any intracellular signal transduction pathway, or any molecular interaction that involves the binding of proteins to DNA (e.g., transcription factor binding to DNA regulatory elements), to lipid mediators (e.g., diacylglycerol activation of protein kinase C), and to nucleotides (e.g., adenosine 3'5'-monophosphate (cAMP) activation of protein kinase A).

In one working example, a method for modulating protein kinase C activity is described. It is hypothesized that the autoinhibitory domain of protein kinase C interacts with the catalytic site so as to inhibit the enzyme activity and this is abolished by the binding of autoinhibitor molecules to the activator binding site thus activating the enzyme. Such autoinhibitory domains, in general, are composed of relatively short peptide sequences. Various synthetic peptides have been made which are modeled on the autoinhibitory domain structure and have been found to show high potency and selectivity against the target enzyme activity. For example, there exists an autoinhibitory peptide of protein kinase C. Since protein kinase C is the target enzyme of tumor promoting phorbol esters, e.g., phorbol esters that activate protein kinase C, it is understood that protein kinase C signalling is involved in oncogenesis. The amino acid sequence of an autoinhibitory peptide of protein kinase C which shows a potent inhibitory activity against protein kinase C is RFARKGALRQKNV (SEQ ID NO:1), which represents residues 19–31 (House et al., *Science* 238:1726–1728, 1987) of protein kinase C. Accordingly, a caged peptide of the 19–31 amino acid sequence is produced by cyclization between the α-amino group of N-terminal residue and the α-carboxyl group.

Like protein kinases, protein phosphatases play an important role for intramolecular signalling and tumor production. Okadaic acid, a potent inhibitor of protein phosphatase type 1 and type 2A, is also known as a potent tumor promoter. Type 1 protein phosphatase is also strongly inhibited by a specific inhibitor protein, protein phosphatase inhibitor 1. Inhibition is achieved when the inhibitor is phosphorylated, and it is known that the inhibitory domain encompasses a phosphorylated amino acid. The inhibitory peptide sequence is IQFTVPLLEPHLDPEAAQIRRRRPTPATLVL (SEQ ID NO:2), where T denotes phosphorylated threonine. Accordingly, caged threonine or caged phosphothreonine is introduced into the sequence during peptide synthesis. Caging of this peptide can also be achieved by cyclization (supra).

Another class of peptides which modify biological activity are peptide hormones such as angiotensin II and endothelin. Such hormones are known to induce cell hypertrophy. The amino acid sequence of angiotensin II is DRVYIHPF (SEQ ID NO:3), cleavage of the precursor peptide DRVYIHPFHL (SEQ ID NO:4) produces the active angiotensin II peptide. Using the techniques described herein, a caged DRVYIHPF peptide can be produced by adding extra amino acid residues at the C-terminus of angiotensin II, e.g., DRVYIHPFG*L, where G* represents 2-nitrophenyl glycine. Upon photolysis, the peptide bond between F and G* is cleaved to release the active angiotensin II.

The effectiveness of any of the aforementioned photosensitive peptides can be tested in any standard animal model system.

Other modifications to the caged peptides or derivatives thereof are also within the invention. For example, a photosensitive caged cytotoxin can be produced using conventional techniques in combination with those methods described herein. Such toxins are useful for inhibiting the development of a neoplasm (e.g., breast cancer). Useful photosensitive cytotoxins are preferably significantly cytotoxic only when present intracellularly and are substantially excluded from any given cell in the absence of a targeting domain. As described below, photosensitive cytotoxins fulfill both of these criteria and are readily synthesized according to the methods described herein.

Potentially useful toxins include, but are not limited to cholera toxin, ricin, 0-Shiga-like toxin (SLT-I, SLT-II, SLT II$_v$), LT toxin, C3 toxin, Shiga toxin, pertussis toxin, tetanus toxin, Pseudomonas exotoxin, saporin, modeccin, gelanin, and tumor necrosis factor. The enzymatically active domain of the cytotoxin, in general, is the domain responsible for cytotoxic activity once the molecule is inside a cell. Accordingly, if desired, this domain is caged and activated only upon illumination. Alternatively, activation of the caged cytotoxin is initiated or inhibited by caging domains of the cytotoxin involved in recognition or translocation, or both.

For example, a useful caged cytotoxin hybrid molecule is formed by synthesizing a photosensitive variant of the enzymatically active A subunit of *E. coli* Shiga-like toxin (see, e.g., Calderwood et al. (1987) *Proc. Natl. Acad. Sci. USA* 84:4364) and fusing this photosensitive variant to the translocation domain (amino acid residues 202 through 460) of diphtheria toxin, and to a receptor. The enzymatically active portion of Shiga-like toxin is released upon photoactivation, and like diphtheria toxin, then acts on the protein synthesis machinery of the cell to prevent protein synthesis, thus killing the cell.

Functional components of such photosensitive cytotoxins of the invention are linked together via a non-covalent or covalent bond, or both. Non-covalent interactions can be ionic, hydrophobic, or hydrophilic, such as interactions involved in a leucine-zipper or antibody-protein G interaction (see, e.g., Derrick et al. (1992) *Nature* 359:752). An example of a covalent linkage is a disulfide bond.

For example, a caged cytotoxin is prepared by chemically conjugating a targeting peptide (or fragment or analog) to any number of known toxic entities, e.g., those described above. Such reactions are carried out by standard techniques known to those skilled in the art. A typical method of conjugating a protein to a protein toxin (including, e.g., bacterial toxins such as diphtheria toxin or Pseudomonas exotoxin A, or plant toxins such as ricin) is by crosslinking through a disulfide bond (see, e.g., Chang et al. (1977) *J. Biol. Chem.* 252:1515) or a heterobifunctional molecule (see, e.g., Cawley et al. (1980) *Cell* 22:563). See also Stevens et al., U.S. Pat. No. 4,894,227.

In general, photosensitive caged agents according to the invention can be administered in a diagnostically or therapeutically effective amount in the form of a pharmaceutically effective acceptable salt such as a hydrochloride, hydrobromide, phosphate, sulfate, acetate, benzoate, or malate. When administered to a mammal for veterinary use, or to a human for clinical, diagnostic, or therapeutic uses, the caged peptide or pharmaceutically acceptable salt thereof can be used alone, or can be combined with any physiologically acceptable carrier such as water, an aqueous solution of normal saline, or any other physiologically acceptable excipient. In general, for example, the dosage range is from 0.001 mg to about 1 mg/kg body weight of the human or animal to be treated.

The caged peptides of the invention or pharmaceutically acceptable salt thereof can be administered e.g., orally, or by injection, e.g., intravenous, intramuscular, or subcutaneous injection. Additionally, if desired, the caged peptides of the invention, or a pharmaceutically acceptable salt thereof, can be administered by a subdermal implant to provide a sustained release of the caged peptide for both diagnostic and therapeutic purposes. Methods well known in the art for making formulations are found in, for example, "Remington's Pharmaceutical Sciences."

Formulations for parenteral administration can, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers can be used to control the release of the compounds. Other potentially useful parenteral delivery systems for the photosensitive caged peptides of the invention include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate and deoxycholate, or can be oily solutions for administration in the form of nasal drops or as a gel.

If desired, treatment with a photosensitive caged molecule of the invention can be combined with more traditional therapies. For example, in the case of cancer treatments, the therapeutic agents of the invention can be used in combination with therapies such as surgery, radiation, or chemotherapy.

In addition, photosensitive caged peptides of the invention can be used for research purposes. Examples of some appropriate research uses for photosensitive caged peptides include studies of signal transduction (e.g., signal transduction mediated by G-proteins, SH-2 domains, calmodulin, protein kinases and protein phosphatases), and studies of other processes mediated by protein-protein interactions such as secretion, ion channel regulation, and excitation-contraction coupling in muscle.

Compounds which have a toxic effect at higher dosages can be administered to a patient as photosensitive caged derivatives using guidelines for administration which will produce greater concentrations of the drugs in the target tissues relative to the surrounding tissue, while maintaining adequate levels of the drug in the target. In general, this differential drug localization can be achieved using guidelines for administration determined using standard techniques known in the field of pharmacology. Determining the appropriate dosage for a patient is a routine matter to one skilled in the art of pharmaceutical administration.

Two approaches are commonly used to assay directly the quantity of an agent in the diseased and surrounding tissues. First, tissue samples are obtained from animals/patients who have received different dosage and timing protocols. The quantity of drug in each tissue is then measured according to standard techniques. The amount of photoactivating irradiation effective in yielding the desired result can be determined using any one of the photoactivating regimes indicated above calibrated to yield a photoactivated molecule within the parameters described above. One skilled in the art can readily determine the optimal photoactivating parameters from within the provided scale for a given cell type, body region, and compound.

Because the drugs administered may have little effect at the provided dosage in the absence of photoactivation, there should be little accompanying generalized toxicity in a patient outside the tissue of interest. Irradiation can be administered either extracorporeally or during surgery. Techniques for both methods of delivery are known to one skilled in the art.

EXAMPLES

To determine the structural requirements necessary for caging amino acids for incorporation into a peptide, several derivatives of a 20-residue peptide (RS-20) were synthesized and their biological activities were compared. RS-20 is an analog of a protein kinase phosphorylation site of myosin light chain kinase shown to be both a high-affinity calmodulin binding peptide and a substrate for cyclic AMP dependent protein kinase (Lukas et al., *Biochemistry* 25: 1458–1464, 1986). The following Examples are intended to illustrate, not limit, the preferred methods for synthesizing the photosensitive compounds of the invention.

Synthesis of RS-20

Solid phase synthesis of RS-20, (Ala-Arg-Arg-Lys-Trp-Gln-Lys-Thr-Gly-His-Ala-Val-Arg-Ala-Ile-Gly-Arg-Leu-Ser-Ser, SEQ ID NO:5), which corresponds to residues 493–512 of the myosin light chain receptor (MCLR), was synthesized according to standard methods. The sequence of RS-20 is shown in FIG. 4A, depicting specific amino acid residues targeted for introducing photosensitive caged amino acids such as glycine, lysine, and tyrosine. FIGS. 4B–4D illustrate such caged amino acids and their corresponding photoproducts.

Synthesis of Caged Amino Groups Containing The 1(2-nitrophenyl)ethyloxycarbonyl Group To develop a general method for caging amino groups selectively on multifunctional molecules, 1(2-nitrophenyl) ethyl chloroformate (V) was synthesized.

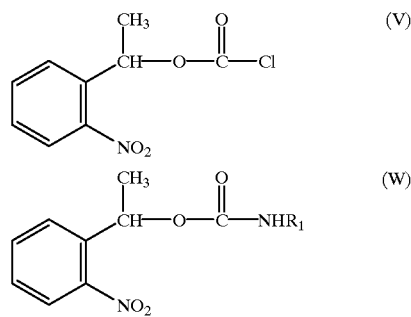

Admixture of 1(2-nitrophenyl)ethanol with 1/3 equivalent of triphosgene in triethylamine yielded compound V ($R_f$=0.88; TLC on silica gel in $CH_2Cl_2$). The product was purified by flash chromatography on silicic acid using methylene chloride as solvent, and $^1$H-NMR in $CDCl_3$ showed loss of —OH protons. Reaction of V with 2 equivalents of monoethanolamine at room temperature for 30 min yielded compound W ($R_1$=$CH_2CH_2OH$; $R_f$=0.38; TLC on silica gel in $CH_2Cl_2$=$CH_3CN$ (2:1); $^1$H-NMR in $CDCl_3$ was consistent with carbamate formation). Reaction of V with f-moc-L-lysine in 2-fold excess under Schotten-Bauman conditions (10% aqueous $Na_2CO_3$/$NaHCO_3$, pH 9) yielded a new compound (W; $R_1$=f-moc-lysine presumably caged on the ε-$NH_2$) that photolyzed to f-moc-L-lysine.

Synthesis of α-carboxyl-2-nitrobenzyl Protecting Group and Its Application

Synthesis of an α-carboxyl 2-nitrobenzyl protecting group was based on the reaction between a phenolic oxygen and compound X containing powdered KOH. 2-Nitromandelate methyl ester (Y) is the starting material for synthesis of α-carboxyl caged phosphate (Walker et al. (1992) *J. Biol. Chem.* 267:2459–2466) and methyl 2-nitromandelate chloroformate.

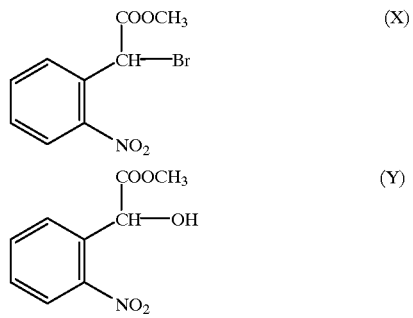

Synthesis of Caged Lysine

Caged f-moc lysine was synthesized by reaction of chloroformate with f-moc-L-lysine under Schotten-Bauman conditions (10% aqueous $Na_2CO_3$/$NaHCO_3$, pH 9). The product, purified by preparative HPLC, was consistent with caged f-moc-L-lysine by $^1$H-NMR, FAB mass spectroscopy and UV spectral analysis. Photolysis regenerated f-moc-Lysine. Caged lysine is shown below.

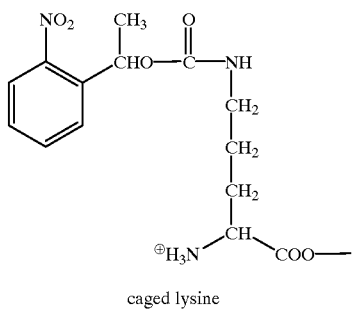

caged lysine

Synthesis of Caged Glycine—2-nitrophenyl glycine

2-Nitrophenyl glycine was synthesized by a four step procedure beginning with 2-nitrophenylacetic acid (Davis et al., 1980). In the first step, this acid was converted to its methyl ester by azeotropic distillation in the presence of benzene, methanol, and $H_2SO_4$. The ester was converted to the α-bromide by refluxing in carbon tetrachloride containing a two-fold stoichiometric excess of N-bromosuccinimide and a catalytic amount of benzoyl peroxide. α-Bromo-2-nitrophenyl acetic acid methyl ester was purified by flash chromatography in hexane:ethyl acetate. The bromide was converted to the amine by coupling to potassium phthalimide in tetrahydrofuran followed by hydrolysis in refluxing 6 N HCl. The product 2-nitrophenyl glycine was purified by preparative reverse phase HPLC on a Magnum ODS-3 column and its identity confirmed by $^1$H-NMR, $^{13}$C-NMR, mass spectrometry and a ninhydrin test.

Synthesis of Caged Tyrosine

α-Carboxy caged tyrosine methyl ester was synthesized beginning with tyrosine t-butyl ester (Sigma, Chemical Co.). A t-BOC group was added to protect the amino function, then the photolabile group, methyl α-carboxyl 2-nitrobenzyl bromide, was coupled to the tyrosine phenolic after treatment with $K^+$ t-butoxide in THF. Purification by flash chromatography was followed by removal of the t-butyl and t-BOC groups by incubation in neat TFA at room temperature. Caged tyrosine is shown below.

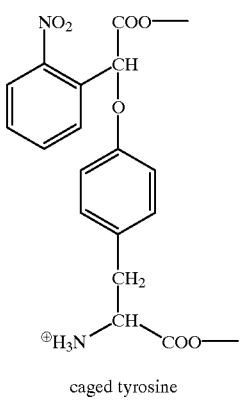

caged tyrosine

Synthesis of Caged Peptides 1-CAG-RS-20 and 9-NPG-RS-20

The synthesis of the RS-20 caged analogs 1-CAG-RS-20 (SEQ ID NO:6) and 9-NPG-RS-20 (SEQ ID NO:7) follows. Other caged analogs of RS-20 and caged analogs of other peptides can be prepared by making appropriate modifications of the following synthetic methods. For peptide synthesis, Fmoc-derivatives of each caged amino acid were utilized, and the peptides 1-CAG-RS-20 and 9-NPG-RS-20 were prepared with 1-CAG-RS-20 containing caged tyrosine at position 5, and 9-NPG-RS-20 containing caged glycine at position 9. Both caged amino acids were synthesized as described above.

Solid-phase peptide synthesis was performed using an automated 12-port Symphony Peptide Synthesizer (Rainin Instruments, Woburn, Mass.). Fluorenylmethoxycarbonyl (Fmoc) methodology was employed with use of Wang resin for C-terminal carboxyl groups and Rink amide resin for C-terminal amides (Novabiochem, La Jolla, Calif.). A double coupling program was used on a scale of 50 μmoles with a 5-fold excess of HBTU-activated [2-(1H-Benzotriazol-1-yl)1,1,3,3-tetramethyluronium hexafluorophosphate] Fmoc-amino acid with 2 equivalents of N-methylmorpholine in N,N-dimethylformamide (DMF).

During each cycle, the N-terminal Fmoc group of the growing peptide chain was removed with 10% piperidine in DMF. The side-chain blocking groups used for each amino acid were: tBu for Ser, Thr and Tyr; OtBu for Asp and Glu; Trt for His, Cys, Asn and Gln; boc for Lys; and Pbf or Pmc for Arg. The resin was swollen in DMF for 3×10 minute and the following program cycle was used for each amino acid in the sequence: 3×30 second washes with DMF; 1×5 minute deblocking with 10% piperidine; 6× washing with DMF; 2×20 minute coupling with HBTU-activated amino acid; 3×30 second washes with DMF.

At the completion of the synthesis, the peptide was cleaved from the resin using the following program: 3× washing with DMF; 2×5 minute deblocking with 10% piperidine; 6× washing with DMF; 6× washing with $CH_2Cl_2$; dry with $N_2$, 1× cleavage for 2 hours; 1× rinse with $CH_2Cl_2$. The cleavage cocktail consisted of the following: trifluoroacetic acid (82.5%), phenol (5%), thioanisole (5%), water (5%), ethanedithiol (2.5%) and triisopropyl-silane (2%). Cleavage was performed automatically by the instrument and collected under $N_2$. The peptide-containing solution (6 ml) was-added to ice-cold diethyl-ether (50 ml) and allowed to precipitate for 30 minutes on ice.

The solution was centrifuged and the pelleted peptide was washed 2 times with diethylether, dissolved in 5% acetic acid, and lyophilized. The peptide was then purified to homogeneity by reverse-phase chromatography on $\mu$-Bondapak C-18 columns (19×300 mm; Waters Associates, Milford, Mass.) using a linear gradient (60 min) from 15% $CH_3CN$ in 0.1% trifluoroacetic acid to 70% $CH_3CN$ at a flow rate of 6 ml/min. Peptides were located by monitoring optical density at 280 m$\mu$ and by ninhydrin staining aliquots on Whatman #1 paper. Regions of the chromatogram were pooled and subjected to amino acid analysis. Criteria of purity included a single peak of optical absorbance, integral molar ratios of the appropriate amino acids and an appropriate molecular weight determined by mass spec analysis.

Binding Characteristics of 1-CAG-RS-20

The 1-CAG-RS-20 was evaluated for its ability to bind a calmodulin agarose column before and after photolysis. This experiment was carried out as follows. 5 mls of calmodulin agarose (Sigma Chemical Co.) was poured into a 1 cm×10 cm glass column and equilibrated with 50 mM Tris pH 7.5, 1 mM CaEGTA, pCa 4.5 (where pCa=−log free $[Ca^{2+}]$. 100 nmoles 1CAGRS-20 in 1 ml of the same solution was loaded onto the column and eluted with the same solution while 14×1.5 ml fractions were collected. The elutant was then changed to 50 mM Tris pH 7.5, 1 mM EGTA, pCa 9 and 14×1.5 ml additional fractions were collected. Each fraction was analyzed for peptide by UV absorbance at 272 nm. A second 100 nmole aliquot of 1-CAG-RS-20 was irradiated by the standard photolysis protocol (see below) and loaded onto the calmodulin agarose column after extensive washing and reequilibration in the original pCa 4.5 solution.

The standard photolysis protocol involves exposure of caged peptide (0.1 to 1 ml; 0.1 mM to 1 mM in 50 mM Tris pH 7.5) in a quartz cuvette (1 cm path length) to the beam of a continuous 75 watt Xenon arc lamp that is filtered through a 300–350 nm band pass filter (UG-11 filter). This standard in vitro photolysis protocol was carried out for 30 minutes at room temperature.

Figure 2:
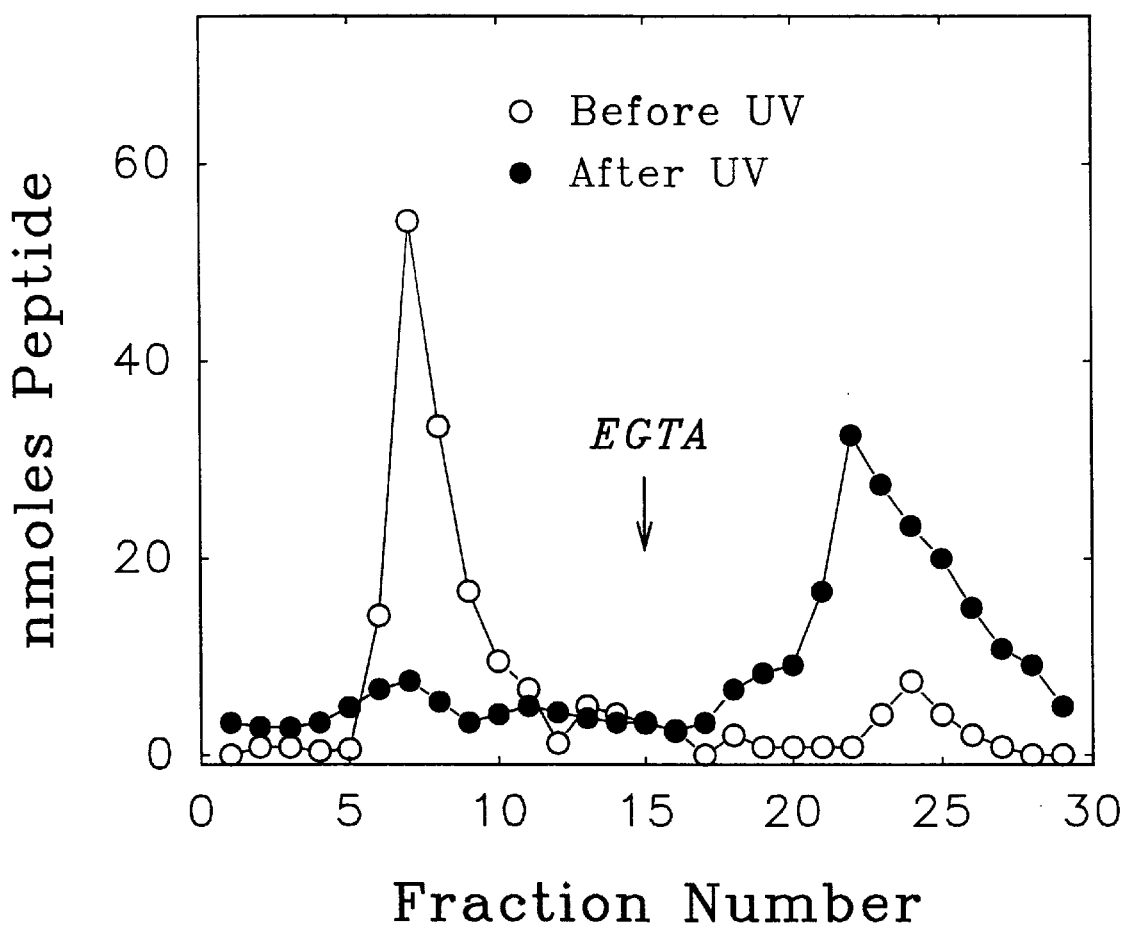
FIG. 2 is two chromatograms showing the binding characteristics to a calmodulin agarose column of a caged tyrosine variant of RS-20 (1-CAG RS-20) before and after UV photolysis.

The results shown in FIG. 2 demonstrate that before photolysis the 1-CAG-RS-20 peptide does not bind appreciably to the column and elutes with the void volume, even in the presence of $Ca^{2+}$. Following photolysis, the peptide binds strongly to the column in the presence of $Ca^{2+}$, but binding is reversed by removal with the $Ca^{2+}$ chelator, EGTA.

Inhibition of Smooth Muscle Myosin Light Chain Kinase (MLCK) Activity

Smooth muscle myosin light chain kinase (MLCK) (0.5 $\mu$g/ml) was incubated with various concentrations of synthetic caged peptide (e.g., 1-CAG-RS-20 and 9-NPG-RS-20) in the presence of 100 nM calmodulin, 0.1 mM $CaCl_2$, 100 mM KCL, 0.2 mg/ml myosin regulatory light chain, 1 mM $MgCl_2$, and 30 mM Tris-HCL (pH 7.5) at 25° C. for 5 minutes. 1-CAG-RS-20 and 9-NPG-RS-20 were photolyzed using the standard photolysis protocol (see above) and the uncaged peptide was purified away from by-products and caged peptides prior to the enzymatic assay using reverse phase HPLC. The phosphorylation reaction was started by adding 50 $\mu$M $^{32}$P-ATP. The incorporation of $^{32}$P into the light chain was measured by scintillation counter and the inhibitory effect of the peptide on myosin light chain kinase was determined.

Biological Activity of 1-CAG-RS-20 and 9-NPG-RS-20

Figure 1:
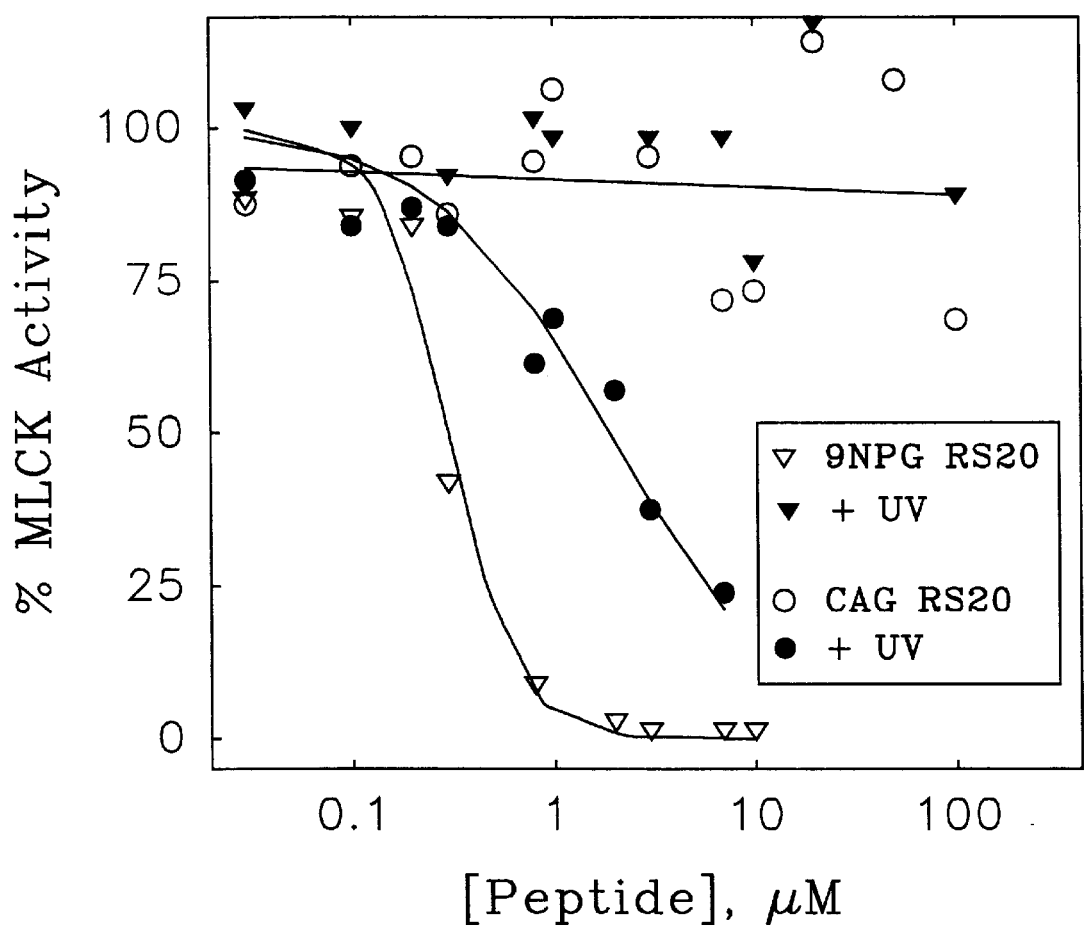
FIG. 1 is a graph showing the effect of caging the $Ca^{2+}$-calmodulin inhibitory peptide, RS-20, before versus after photolysis on myosin light chain kinase activity (a caged tyrosine variant of RS-20, 1-CAG-RS-20 (-○-), photolysed 1-CAG-RS-20 (-●-); a caged glycine variant of RS-20, 9-NPG-RS-20 (-▽-), photolysed 9-NPG-RS-20 (-▼-)).

The purified caged RS-20 peptides, 1-CAG-RS-20 and 9-NPG-RS-20, before and after photolysis were evaluated in above-described assay for the ability to inhibit MLCK activity. The results presented in FIG. 1 show that 1-CAG-RS-20 (SEQ ID NO:6) before photolysis failed to significantly inhibit MLCK activity. However, it can be seen that photolyzed 1-CAG-RS-20 inhibited MLCK activity by greater than 50% at 10 $\mu$M. These results show that modification of RS-20 with a caged tyrosine at position 5, i.e., 1-CAG-RS-20, produces a molecule lacking biological activity prior to photolysis, which is subsequently rendered biologically active upon photolysis and removal of the caging group.

The results in FIG. 1 also show that RS-20, which has a photolabile 2-nitrophenyl glycine incorporated at position 9, is biologically active, inhibiting MLCK activity to less than 10% over a range of concentrations. Furthermore, the results demonstrate that upon photolysis, 9-NPG-RS-20 is rendered biologically inactive. In this case, photolysis of 9-NPG-RS-20 results in site-specific cleavage of the peptide backbone of RS-20, rendering the molecule inactive.

Effects of 1-CAG-RS-20 on Calcium-dependent Enhancement of Calcium Current in Smooth Muscle The in vivo effects of 1-CAG-RS-20 on calcium-dependent enhancement of calcium current in smooth muscle were evaluated according to the methods described by McCarron et al. (*Nature* 357: 74–77). Photolysis of 1-CAG-RS-20 was accomplished by selectively exposing cells to a beam of UV irradiation using a light source fitted with a controllable shutter. In addition, experiments were carried out by recording phase contrast images in the far red portion of the spectrum to monitor the effects of 1-CAG-RS-20 on the contractile responses of the cells to $Ca^{2+}$ influx resulting from depolarization. Data was analyzed according to the methods described in Itoh et al. (*Nature* 338: 164–167, 1989).

As shown in FIG. 3C, the cell was depolarized with a depolarizing pulse for −100 to +10 mV for 3 seconds, then a train of depolarizing pulses at a frequency of 2 pulses per second for 8 seconds was applied, and then after 12 seconds, a pulse similar to the first depolarization was applied. Shown in these panels (FIG. 3) are the inward currents resulting from depolarization both before and after the train of depolarizing pulses. The trace labelled #1 was obtained before the train and that after the train is labelled #2 (FIG. 3C).

As can be seen in FIG. 3A, the magnitude of the inward current triggered by the second pulse was enhanced relative to that of the first pulse prior to the train. As shown in FIG. 3B, this enhancement was observed even after the cell was exposed to ultraviolet light of the same duration and intensity used to uncage the peptide. FIGS. 3A and 3B show results for a single cell not injected with the caged 1-CAG-RS-20 peptide. FIG. 3C shows currents recorded in a single smooth muscle cell injected with 1-CAG-RS-20. Prior to exposure to ultraviolet light, as can be seen in FIG. 3C, the inward current was enhanced following the train of depolarizing stimuli. By contrast, as shown in FIG. 3D, enhancement of the inward current typically observed following a train of depolarizing stimuli was blocked following photolysis of 1-CAG-RS-20.

Effects of 1-CAG-RS-20 on Calcium-Mediated Smooth Muscle Cell Contraction

The in vivo effects of 1-CAG-RS-20 (200 μM) on the rate of shortening of single smooth muscle cells both before and after UV exposure was performed essentially as described in Itoh et al. (*Nature* 338: 164–67, 1989). Images of the cells were recorded using phase contrast optics and measurements of cell length were carried out as described by Itoh et al., supra. An interactive computer analysis program was used to measure cell length at successive intervals after the onset of cell membrane depolarization and subsequent increase in cytoplasmic $Ca^{2+}$ concentration that normally triggers contraction. The results presented in FIG. 5 show that toad muscle cells shortened more slowly after photolysis of 1-CAG-RS-20 (SEQ ID NO:6) than without photolysis, indicating that the uncaged RS-20 peptide inhibited the contractile response of the toad stomach cells.

OTHER EMBODIMENTS

It should be understood that the examples and embodiments described herein are for illustrative purposes only and that various modifications or changes in light thereof are within the scope of the appended claims.

We claim:

1. A method for preparing a photosensitive peptide comprising the steps of:

(a) obtaining a photolabile amino acid comprising a photolabile group bonded to a side chain of an amino acid; and (b) incorporating said photolabile amino acid into a peptide during synthesis of said peptide, wherein incorporation of said photolabile amino acid into said peptide yields a photosensitive peptide which is biologically activatable or deactivatable upon irradiation in a biological system, and wherein (c) said photosensitive peptide is synthesized chemically using solid-phase or solution-phase coupling of amino acids.

2. A method of claim 1, wherein said photolabile group is 2-nitrobenzyloxycarbonyl.

3. A method of claim 1, wherein said photolabile group is α-carboxy 2-nitrobenzyl.

4. A method of claim 1, wherein said photolabile group is 2-nitrophenylethyl.

5. A method of claim 1, wherein said amino acid is lysine.

6. A method of claim 1, wherein said amino acid is tyrosine.

7. A method of claim 1, wherein said amino acid is glycine.

8. A method of claim 1, wherein said photosensitive peptide is biologically inactive and is biologically activated upon irradiation.

9. A method of claim 1, wherein said photosensitive peptide is biologically active and is biologically inactivated upon irradiation.

10. A method of claim 1, wherein said amino acid is selected from the group consisting of serine, threonine, histidine, glutamine, asparagine, aspartic acid, glutamic acid, and combinations thereof.

11. The method of claim 1, wherein said photolabile amino acid has the formula

wherein X is any amino acid which is bonded via its side chain to Z, Z is

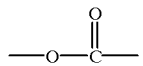

or is absent, and Y has the formula

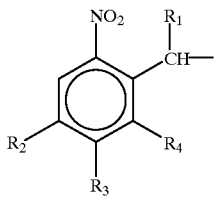

wherein, independently, $R_1$ is —H, —CH$_3$, —CONH$_2$ or —COO$^-$; and $R_2$, $R_3$, and $R_4$ are, independently, —H, —CH$_3$, —OCH$_3$, —CH$_2$COO$^-$, —OH, or —NO$_2$.

12. A method of introducing a photosensitive cleavage site into a synthetic peptide, the method comprising chemically synthesizing a synthetic peptide comprising at least one photolabile glycine residue, wherein said photolabile glycine residue includes a photolabile group bonded to its α-carbon, and wherein upon irradiation said synthetic peptide is cleaved along its peptide backbone at a position in said synthetic peptide occupied by said photolabile glycine residue.

13. A method of claim 12, wherein said photolabile glycine residue has the formula

wherein X is glycine which is bonded via its α-carbon to Y, and Y has the formula

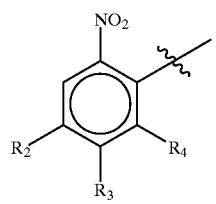

wherein $R_2$, $R_3$, and $R_4$ are, independently, —H, —CH$_3$, —OCH$_3$, —CH$_2$COO$^-$, —OH, or —NO$_2$.

14. A method of claim 13, wherein said photolabile glycine residue is 2-nitrophenyl glycine (NPG).

15. A self-cleaving photosensitive synthetic peptide comprising at least one photolabile glycine residue having a photolabile group bonded to its α-carbon, wherein upon irradiation said synthetic peptide is cleaved at a position in said synthetic peptide occupied by said photolabile glycine residue.

16. A photosensitive synthetic peptide of claim 15, wherein said photolabile glycine residue has the formula

wherein X is glycine which is bonded via its α-carbon to Y, and Y has the formula

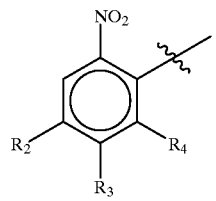

wherein $R_2$, $R_3$, and $R_4$ are, independently, —H, —CH$_3$, —OCH$_3$, —CH$_2$COO$^-$, —OH, or NO$_2$.

17. A photosensitive synthetic peptide of claim 15, wherein said photolabile glycine residue is 2-nitrophenyl glycine (NPG).

* * * * *

```
                          SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:1:

Arg Phe Ala Arg Lys Gly Ala Leu Arg Gln Lys Asn Val
1               5                   10

(2) INFORMATION FOR SEQ ID NO:2:

(i) SEQUENCE CHARACTERISTICS:
        (A) LENGTH: 31 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:2:

Ile Gln Phe Thr Val Pro Leu Leu Glu Pro His Leu Asp Pro Glu Ala
1               5                   10                  15

Ala Gln Ile Arg Arg Arg Arg Pro Thr Pro Ala Thr Leu Val Leu
                20                  25                  30

(2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: both (ii) MOLECULE TYPE: protein (xi) SEQUENCE DESCRIPTION: SEQ ID NO:3:

Asp Arg Val Tyr Ile His Pro Phe
1               5

(2) INFORMATION FOR SEQ ID NO:4:

(i) SEQUENCE CHARACTERISTICS:
        (A) LENGTH: 10 amino acids
```

```
            (B) TYPE: amino acid
            (C) STRANDEDNESS: Not Relevant
            (D) TOPOLOGY: both (ii) MOLECULE TYPE: protein (xi) SEQUENCE DESCRIPTION: SEQ ID NO:4:

Asp Arg Val Tyr Ile His Pro Phe His Leu
1               5                   10

(2) INFORMATION FOR SEQ ID NO:5:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: both (ii) MOLECULE TYPE: protein (xi) SEQUENCE DESCRIPTION: SEQ ID NO:5:

Ala Arg Arg Lys Trp Gln Lys Thr Gly His Ala Val Arg Ala Ile Gly
1               5                   10                  15

Arg Leu Ser Ser
            20

(2) INFORMATION FOR SEQ ID NO:6:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: both (ii) MOLECULE TYPE: protein (ix) FEATURE:
            (D) OTHER INFORMATION: Xaa at position 5 contains a caged
                tyrosine.

(xi) SEQUENCE DESCRIPTION: SEQ ID NO:6:

Ala Arg Arg Lys Xaa Gln Lys Thr Gly His Ala Val Arg Ala Ile Gly
1               5                   10                  15

Arg Leu Ser Ser
            20

(2) INFORMATION FOR SEQ ID NO:7:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: both (ii) MOLECULE TYPE: protein (ix) FEATURE:
            (D) OTHER INFORMATION: Xaa at position 9 contains a caged
                glycine.

(xi) SEQUENCE DESCRIPTION: SEQ ID NO:7:

Ala Arg Arg Lys Trp Gln Lys Thr Xaa His Ala Val Arg Ala Ile Gly
1               5                   10                  15

Arg Leu Ser Ser
            20
```